(12) United States Patent
Lutz et al.

(10) Patent No.: US 11,709,145 B2
(45) Date of Patent: Jul. 25, 2023

(54) SENSOR ASSEMBLY

(71) Applicant: Roche Diagnostics Operations, Inc., Indianapolis, IN (US)

(72) Inventors: Sascha Lutz, Neustadt (DE); Gregor Ocvirk, Frankfurt (DE); Christoph Boehm, Viernheim (DE); Wolfgang Burkhardt, Cham (CH); Miriam Ruf, Mannheim (DE); Heinz Kontschieder, Graz (AT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 17/643,463

(22) Filed: Dec. 9, 2021

(65) Prior Publication Data
US 2022/0196584 A1    Jun. 23, 2022

(30) Foreign Application Priority Data
Dec. 21, 2020    (EP) ..................................... 20215881

(51) Int. Cl.
*G01N 27/06*    (2006.01)
*G01N 33/487*    (2006.01)

(52) U.S. Cl.
CPC ....... *G01N 27/06* (2013.01); *G01N 33/48707* (2013.01)

(58) Field of Classification Search
CPC .......................... G01N 27/06; G01N 33/48707
USPC ........................................................ 324/693
See application file for complete search history.

(56) References Cited

U.S. PATENT DOCUMENTS

| | | | | |
|---|---|---|---|---|
| 5,004,583 A | * | 4/1991 | Guruswamy | ...... G01N 27/4165 422/408 |
| 5,074,157 A | * | 12/1991 | Marsoner | ......... G01N 33/48707 73/864.81 |
| 7,223,364 B1 | * | 5/2007 | Johnston | ........... B01L 3/502746 422/68.1 |

(Continued)

FOREIGN PATENT DOCUMENTS

| | | | |
|---|---|---|---|
| CA | 2971921 A1 | * 12/2006 | ............ B01L 3/5027 |
| EP | 1362827 B1 | * 9/2008 | ........ B01L 3/502707 |

(Continued)

OTHER PUBLICATIONS

European Search Report dated Oct. 21, 2021, in Application No. 20215881.2, 3 pp.

*Primary Examiner* — Jermele M Hollington
*Assistant Examiner* — Sean Curtis
(74) *Attorney, Agent, or Firm* — Roche Diagnostics Operations, Inc.

(57) ABSTRACT

The present disclosure refers to a sensor assembly for an IVD analyzer, the sensor comprising two opposite substrates with at least one fluidic conduit for receiving a sample. The electrodes of different types of electrochemical sensors are arranged on the two opposite substrates facing the at least one fluidic conduit for coming in contact with the sample and determining sample parameters, wherein the counter electrodes and the reference electrodes are formed on one substrate and the working electrodes are formed on the opposite substrate. This achieves optimal sensor-working conditions in terms of a homogeneous and symmetrical electric field density and enables a sensor assembly with simpler geometry and smaller size.

14 Claims, 3 Drawing Sheets

(56) References Cited

U.S. PATENT DOCUMENTS

| | | | |
|---|---|---|---|
| 7,261,824 B2* | 8/2007 | Schlautmann | B81C 1/00119 |
| | | | 216/2 |
| 7,341,834 B2* | 3/2008 | Yang | G01N 27/3277 |
| | | | 435/6.12 |
| 7,998,666 B2* | 8/2011 | Stiene | G01N 33/5438 |
| | | | 427/209 |
| 8,197,775 B2* | 6/2012 | Johnston | B01L 3/5023 |
| | | | 422/402 |
| 8,420,313 B2* | 4/2013 | Yang | G01N 27/3277 |
| | | | 422/68.1 |
| 8,728,288 B2* | 5/2014 | Aas | G01N 33/4915 |
| | | | 204/411 |
| 9,731,297 B2* | 8/2017 | Glezer | B01L 7/525 |
| 10,533,994 B2* | 1/2020 | Holmes | A61B 5/150755 |
| 10,761,030 B2* | 9/2020 | Holmes | G01N 33/53 |
| 10,782,232 B2* | 9/2020 | Stevanovic | G01N 21/4785 |
| 10,814,327 B2* | 10/2020 | Glezer | B01L 7/525 |
| 10,981,172 B2* | 4/2021 | Vandersleen | B01L 7/00 |
| 11,016,053 B2* | 5/2021 | Huff | G01N 33/54326 |
| 11,237,161 B2* | 2/2022 | Khattak | B01L 3/5029 |
| 11,287,421 B2* | 3/2022 | Holmes | A61B 5/150854 |
| 2003/0201194 A1* | 10/2003 | Heller | A61B 5/1411 |
| | | | 204/403.14 |
| 2003/0226604 A1* | 12/2003 | Schlautmann | B01L 3/502707 |
| | | | 137/827 |
| 2004/0021469 A1* | 2/2004 | Blomberg | G01N 33/491 |
| | | | 324/434 |
| 2004/0055898 A1* | 3/2004 | Heller | A61B 5/1486 |
| | | | 205/777.5 |
| 2005/0164322 A1* | 7/2005 | Heller | A61B 5/150358 |
| | | | 435/14 |
| 2007/0287191 A1* | 12/2007 | Stiene | G01N 27/3272 |
| | | | 427/209 |
| 2008/0017522 A1* | 1/2008 | Heller | C12Q 1/006 |
| | | | 600/300 |
| 2008/0194990 A1* | 8/2008 | Heller | C12Q 1/004 |
| | | | 600/583 |
| 2008/0277291 A1* | 11/2008 | Heller | A61B 5/14865 |
| | | | 204/403.01 |
| 2011/0297555 A1* | 12/2011 | Stiene | A61B 5/1486 |
| | | | 156/217 |
| 2013/0220820 A1* | 8/2013 | Pamidi | C12Q 1/003 |
| | | | 205/115 |
| 2014/0048481 A1* | 2/2014 | Shih | G01N 30/466 |
| | | | 427/256 |
| 2014/0263279 A1* | 9/2014 | Vandersleen | B01L 7/00 |
| | | | 219/494 |
| 2018/0275088 A1* | 9/2018 | Huff | B01L 3/502761 |
| 2021/0325334 A1* | 10/2021 | Huff | G01N 33/54326 |
| 2022/0196584 A1* | 6/2022 | Lutz | G01N 27/27 |
| 2022/0196632 A1* | 6/2022 | Boehm | A61B 5/1468 |
| 2022/0280937 A1* | 9/2022 | Schlaminger | G01N 33/487 |

FOREIGN PATENT DOCUMENTS

| | | | | |
|---|---|---|---|---|
| EP | | 1997772 A2 * | 12/2008 | ........ B01L 3/502707 |
| EP | | 1546698 B1 * | 12/2013 | ........... G01N 33/491 |
| EP | | 3988642 A1 * | 4/2022 | |
| JP | | S62-14141 A | 1/1987 | |
| JP | | 2011-099867 A5 | 6/2011 | |
| JP | | 2022098478 A * | 7/2022 | ............. G01N 27/06 |
| WO | | 1987/000286 A1 | 1/1987 | |
| WO | | 1992/005449 A1 | 4/1992 | |
| WO | WO-2005119200 A1 * | | 12/2005 | ........ B01L 3/502707 |
| WO | WO-2006015615 A1 * | | 2/2006 | ........... A61B 5/1486 |

* cited by examiner

SENSOR ASSEMBLY

CROSS-REFERENCE TO RELATED APPLICATIONS

This application claims priority to European Patent Application No. 20215881.2 filed 21 Dec. 2020, the disclosure of which is hereby incorporated by reference in its entirety.

TECHNICAL FIELD

The present disclosure relates to a sensor assembly for an IVD analyzer that comprises sensors arranged in fluidic conduits for determining sample parameters in a sample.

BACKGROUND

In-vitro diagnostic (IVD) analyzers such as blood gas and electrolyte analyzers can be used in critical care units, in the emergency room, in the hospital ward, in surgery units, in anesthesia, in outpatient clinics, in medical practices or during transport of patients. These are typically point of care settings, where there is a demand for short turn-around-times (TAT or STAT) of diagnostic results and/or where it is required to take multiple samples from a patient in short succession.

In blood gas and electrolyte testing, parameters are determined from a patient's sample, like the partial pressure of blood gases ($PO_2$, $PCO_2$), oxygen saturation ($SO_2$), the pH value, electrolyte concentrations (e.g., $Na^+$, $K^+$, $Mg^{2+}$, $Ca^{2+}$, $Li^+$, $Cl^-$), bicarbonate values ($HCO_3^-$), the concentration of metabolites (e.g., glucose, lactate, urea, creatinine), values for hemoglobin and hemoglobin derivatives (e.g., tHb, $O_2$Hb, HHb, COHb, MetHb, SulfHb), bilirubin values, and hematocrit. These parameters allow a physician to obtain important information on heart function, lung function and kidney function of the patient.

Currently, a number of IVD analyzers are available on the market, which allow for measurements of these parameters with different degrees of automation. Generally, the parameters are determined by conductivity, electrochemical and/or optical measuring principles. In the latest generations of these IVD analyzers, the sensors required for these measuring principles are combined in a multi-use sensor assembly, to be inserted into an IVD analyzer. This allows for simultaneous determination of a plurality of parameters from one single sample in one single measurement. It is usually a goal to use the same sensor assembly for as many measurements as possible. However, when required, e.g., if one or more of the sensors reach the end of their in-use time, the sensor assembly can be replaced with a new one.

The measurements take place in measuring chambers arranged inside the sensor assembly. These chambers can be designed as fluidic conduits, which are equipped with the respective conductivity, electrochemical, and/or optical sensors. In order to perform a measurement, a sample is introduced into the fluidic conduit so that it comes into contact with the sensors. After the measurement, the sample is removed from the fluidic conduit and replaced by other fluids, e.g., a stand-by solution, a wash fluid, a quality control (QC) sample, a subsequent sample, a calibrator, etc.

Measurements are usually performed on whole blood samples, ideally on arterial blood samples. The collection of arterial blood however is especially burdensome for patients. In certain patient groups, e.g., in neonates, capillary blood samples are drawn. This means that only limited volumes of sample material are available. It is therefore a general trend in blood gas and electrolyte testing to arrange as many sensors as possible into a sensor assembly and to minimize the size of the measuring chamber. This enables obtaining as many parameters as possible from one single sample, thus reducing the burden of sample collection for the patient, and enables handling of small sample volumes.

Advancements in the field of integrated circuit technology have made possible the development of ever smaller sensors, e.g., by using thick-film or thin-film technologies, allowing for a minimization of the overall sensor assembly size. Also, sensor arrangements and sensor assembly geometries have advanced. For example, U.S. Pat. No. 8,728,288 B2 discloses a sensor assembly, in which fully functional analyte sensors are placed on opposing walls of a measuring chamber, allowing smaller sample volumes to be used without reducing the number of sensors in the sensor assembly. The sensor distribution as presented in said disclosure however cannot fully exclude possible interferences between sensors. Also, the electrodes that form these sensors may degrade asymmetrically due to the sensors' planar arrangement and the resulting lateral flow of sensor current.

Additionally, it can be advantageous to increase the in-use time of sensor assemblies. Replacing a sensor assembly with a new one leads to a downtime of the IVD analyzer, including the time during which the new sensor assembly requires initialization. Frequent sensor assembly replacement therefore represents a disadvantage in regard of economic efficiency, usability, sample throughput, time-to-result, and waste production.

SUMMARY

It is against the above background that the embodiments of the present disclosure provide certain unobvious advantages and advancements over the prior art. In particular, a need was recognized for improvements of a sensor assembly for in-vitro diagnostic (IVD) analyzers.

Although the embodiments of the present disclosure are not limited to specific advantages or functionality, it is noted that the present disclosure allows for a sensor assembly that enables fast, precise, interference-free, and reliable determination of a plurality of parameters from one single sample, with a small sample volume, without reducing the number of sensors in the assembly and consequently without reducing the number of possible parameters to be measured from a sample. This is achieved by arranging the electrodes of electrochemical sensors in a particular manner on two opposite substrates. Another advantage of this arrangement is the achievement of optimal sensor-working conditions, e.g., enabling a homogeneous and symmetrical current density and field distribution on the electrode surface Another advantage of the sensor assembly according to the present disclosure is that manufacturing of the sensor assembly with the respective arrangement of electrochemical sensors is simpler and more cost-effective. For example, if defective electrodes are detected during the manufacturing procedure, only the effected substrates need to be discarded instead of the entire sensor assembly, thus increasing the yield and lowering manufacturing costs. Further, certain sensor types or certain sensory elements, e.g., reference electrodes or counter electrodes, have a simpler design compared to others, e.g., working electrodes. It has proven to be advantageous when sensors or electrodes with similar structures and similar manufacturing procedures are manufactured on the same substrate.

Another advantage of the sensor assembly according to certain embodiments is that the sensor assembly's in-use time can be further extended, thereby reducing the number of sensor assembly exchanges and consequently reducing the downtime of the IVD analyzer during sensor assembly installation and initialization. This also improves usability in terms of ease and convenience of use.

Another advantage of the sensor assembly according to certain embodiments is that it enables a temperature-controlled measurement of the sample.

In particular, the present disclosure describes a sensor assembly for an IVD analyzer comprising two opposite substrates with at least one fluidic conduit formed in between for receiving a sample. The sensor assembly further comprises a plurality of electrochemical sensors arranged on the two opposite substrates facing the at least one fluidic conduit for coming in contact with the sample and determining sample parameters. The plurality of electrochemical sensors are chosen from the groups of amperometric sensors, potentiometric sensors or combinations thereof, wherein a potentiometric sensor comprises a potentiometric working electrode (PWE) and a potentiometric reference electrode (PRE), and wherein an amperometric sensor comprises an amperometric working electrode (AWE) and an amperometric counter reference electrode (ACRE) or an AWE and an amperometric reference electrode (ARE) and an amperometric counter electrode (ACE). The PRE(s) and/or the ACRE(s) and/or the ARE(s) and the ACE(s) are thereby formed on the same one of the two substrates, whereas the PWE(s) and/or the AWE(s) are formed on the opposite one of the two substrates.

These and other features and advantages of the embodiments of the present disclosure will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present description can be best understood when read in conjunction with the following drawings, where like structure is indicated with like reference numerals and in which.

Figure 1:
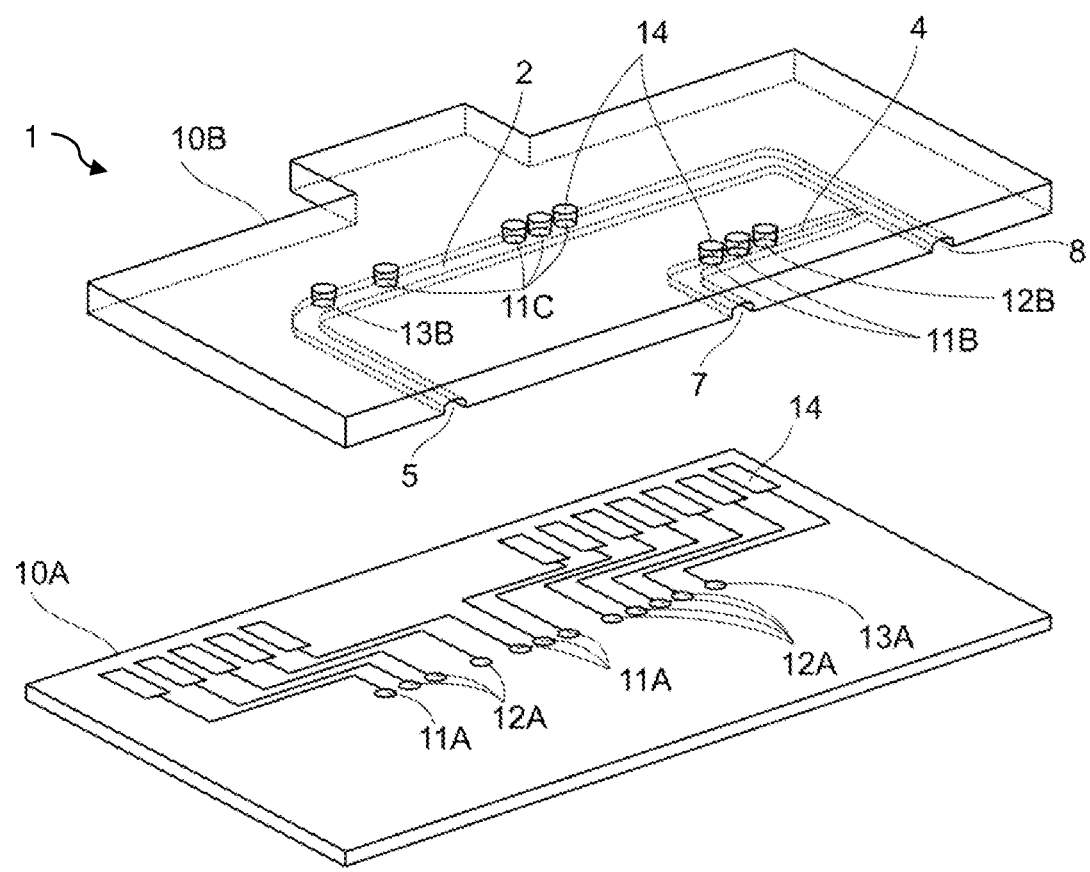
FIG. 1 is a schematic three-dimensional exploded-view of a sensor assembly according to an embodiment comprising two opposite substrates in accordance with an embodiment of the present disclosure.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiments of the present disclosure.

DETAILED DESCRIPTION

The term "IVD analyzer" as used herein refers to an automated or semi-automated analytical apparatus configured to examine samples in vitro in order to provide information for screening, diagnosis and treatment monitoring purposes. The IVD analyzer is designed and adapted to the medical area of application, the parameters to be determined and corresponding laboratory workflows. For example, in a point-of-care testing environment, IVD analyzers can vary from handheld devices with low throughput, short turn-around time and limited number of measurable parameters to compact benchtop instruments with higher throughput and higher number of measureable parameters. Such IVD analyzers are designed to detect certain types of parameters, e.g., gases, electrolytes, metabolites, clinical chemistry analytes, immunochemistry analytes, coagulation parameters, hematology parameters, etc. Depending on the parameters of interest, a variety of different analytical methods and different detection technologies can be applied. For example, in the field of blood gas and electrolyte testing, electrochemical measuring principles and/or conductivity measuring principles and/or optical detection methods are used. An IVD analyzer comprises a plurality of functional units, each dedicated to a specific task and cooperating with each other in order to enable automated sample processing and analysis. Such functional units may be, e.g., a fill port for receiving a sample, a pump, a valve, an analytical measurement unit, an optical detection unit, a hemolysis unit, a sample injection nozzle, a reagent storage, a temperature regulating unit, a controller, etc. One or more functional units may be integrated into a larger unit or module in order to simplify the operation of the IVD analyzer. An example of such a module is a fluid pack that combines a fill port for receiving a sample, optical detection units, a fluid system, pumps, valves, pouches with system fluids, etc., that can be exchanged if required. Such an exchangeable module is also considered as part of the IVD analyzer in this disclosure, even if it is not a permanently installed part.

The term "sensor" is herein generically used to indicate a detector configured to detect sample parameters by generating a correlated signal output that can be quantified and digitized. The sensor can be a biosensor, a chemical sensor or a physical sensor, and is typically a part of a functional unit of an IVD analyzer, e.g., an analytical measurement unit. The sensor can be selective or specific with respect to one sample parameter of interest or can be configured to detect and quantify a plurality of different sample parameters of interest. Depending on the type of sensor, a sensor can comprise a plurality of sensory elements. The term "sensory element" therefore refers to a part of a sensor (e.g., a working electrode, a reference electrode, a counter electrode) that in combination with one or more other sensory elements forms a fully functional sensor.

The term "sensor assembly" as used herein refers to a functional unit comprising more than one sensor, where the sensors may be of the same type, e.g., based on the same functional principle and/or sensor design, or may be of a different type. The sensor assembly is typically designed as an exchangeable multi-use unit. However, the term "sensor assembly" as used herein may also refer to a functional unit that is permanently installed in an IVD analyzer. Typically, several hundred samples can be measured with one sensor assembly before it reaches the end of its in-use time. The sensors of the sensor assembly are typically applied to substrates, where substrates are planar elements capable of carrying the necessary wiring for connecting the sensors with electrical contact elements. These electrical contact elements are required to establish electrical connection with the IVD analyzer. A substrate has two major surface areas, whereby all sensors that are applied to the substrate are typically applied to the same major surface area. A sensor assembly may be designed to comprise two substrates that are arranged opposite to each other, so that the major surface areas carrying the sensors face each other. The two opposite substrates can be arranged in parallel or they can be arranged at an inclination angle relative to each other (e.g., at an angle between 0° and 1°, or at an angle between 0° and 2°, or at an angle between 0° and 5°). A substrate can be made of either an electrically non-conducting material, e.g., a polymer, ceramic, glass, or of a conducting material, e.g., metals like steel, aluminum, platinum, gold, or metal alloys. In the latter case, an insulation layer, e.g., a polymer layer or an epoxy resin, is applied between the sensor and the conductive substrate. The sensor assembly can be constructed so that two opposite substrates are in a permanently fixed position relative to each other. A substrate can further be in contact with a thermally conductive element, e.g., a metal or metal alloy element, or the substrate can be thermally conductive itself, e.g., a steel substrate. This allows for temperature exchange with a temperature-regulating unit of the IVD analyzer, e.g., a heating coil or a Peltier element. A sensor assembly may be designed as a functional unit that is permanently installed in an IVD analyzer or it may be designed as an exchangeable consumable. It may further comprise a housing to protect the sensors and wiring from external influences and to facilitate handling. The housing can be made of any non-conductive material to prevent influences on the electrochemical measurements.

A sensor assembly further comprises at least one fluidic conduit formed in-between the two opposite substrates for receiving a sample, in order to bring it in contact with the available sensors. The fluidic conduit can be constructed as a recess either within one substrate or partially in a substrate and partially in the opposite substrate, where the sensors are arranged on the substrates such that they face the recess in order to come in contact with an introduced sample. The two opposite substrates may further be divided into subunits, where each subunit carries at least one sensor or electrode, and where the at least one fluidic conduit is formed as continuous fluidic conduit across the subunits. According to an embodiment, the at least one fluidic conduit is formed in a spacer arranged between the two opposite substrates. The spacer is a planar element that is arranged in-between and in parallel to the two opposite substrates. The height of the spacer is determined based on the required cross-sectional area of the fluidic conduit. Typically, the height of the spacer is comprised between 10 and 700 um, e.g., between 50 and 600 um, or between 70 and 500 um. In order to prevent leakage of the introduced fluid, a sensor assembly may comprise sealing element(s) for sealing the fluidic conduit. Depending on the design of the sensor assembly, the sealing element can be positioned between the two opposite substrates or between each of the substrates and the spacer. The spacer itself may alternatively act as a sealing element as well.

A sensor assembly may comprise a plurality of physically separated fluidic conduits, i.e., each fluidic conduit having a separate fluidic inlet and fluidic outlet, or it may comprise a plurality of fluidic conduits that converge inside the sensor assembly and at least partially share a common fluidic pathway (e.g., a common fluidic inlet and/or a common fluidic outlet). Even though they are fluidically connected in the latter case, the fluidic conduits are referred to as separate fluidic conduits in this disclosure, because the common pathways are usually not critical for obtaining measurement results. With other words, the areas where sensors are present and measurements are conducted are spatially separated from each other. Further, fluidic conduits may differ in their function despite existing fluidic connections. For example, a reference fluidic conduit is a fluidic conduit intended for conducting reference measurements in a reference solution, as opposed to a fluidic conduit intended for detecting parameters in a biological sample. Nevertheless, such a fluidic conduit and the reference fluidic conduit may share a common fluidic outlet.

The term "sample" as used herein is a generic term to indicate any type of material that is processed in an IVD analyzer. It may refer to, e.g., a biological sample, to liquids that contain known levels of analytes and are used to confirm the IVD analyzer's operability, e.g., a quality control (QC) sample or a calibrator or a reference solution, or to liquids that are used to bring or maintain the IVD analyzer in an operating mode, e.g., a stand-by solution/rinse solution or a wetting solution.

A "biological sample" refers to any biological material suspected of containing one or more analytes whose detection—qualitative and/or quantitative—may be associated to a medical condition. It can be derived from any biological source, such as a physiological fluid, including, blood, saliva, sputum, ocular lens fluid, cerebral spinal fluid (CSF), sweat, urine, milk, ascites fluid, mucous, synovial fluid, peritoneal fluid, pleural fluid, amniotic fluid, tissue, bone marrow, feces, cells or the like. The biological sample may be used directly as obtained from the source or following a pretreatment and/or sample preparation workflow to modify the character of the biological sample, such as preparing plasma from blood, diluting viscous fluids, lysis or the like. Methods of treatment can involve filtration, centrifugation, dilution, concentration, inactivation of interfering components, and the addition of reagents, e.g., to enable carrying out one or more in-vitro diagnostic tests. The term "sample" is therefore not necessarily used to indicate the original sample but may also relate to a sample that has already been processed (pipetted, diluted, mixed with reagents, enriched, purified, amplified, etc.).

A "QC sample" refers to a sample material that mimics a biological sample and that contains known values of one or more QC substances. Typically, QC samples are supplied in one or more levels, e.g., two or three levels that correspond to different concentration ranges of the QC substances. QC samples are typically measured in the same way and under the same conditions as biological samples, in order to check that a calibrated sensor is actually within the specifications or admissible range. A "QC substance" can be an analyte identical to an analyte of interest, the concentration of which is known, or that generates by reaction an analyte identical to an analyte of interest, the concentration of which is known, e.g., $CO_2$ from bicarbonate, or it can be any other equivalent substance of known concentration, which mimics the sample parameter of interest or that can be otherwise correlated to a certain parameter of interest, e.g., a dye that behaves optically similar to hemoglobin or bilirubin.

A "calibrator" is a calibration solution that contains known values of one or more calibration materials used for calibration and that is measured under the same conditions as a biological sample. Typically, one or two calibrators are used for a one-point or two-point calibration respectively, when the sensor responds linearly to analyte concentrations. Three or more calibrators may be used if the calibration curve is non-linear. In particular, also calibrators can be provided in different levels that correspond to different concentration ranges of the QC materials. A calibration material can be the same as a QC substance.

A "reference solution" is a standard solution such as a calibrator, with known analyte concentration, that may be used for calibration, and that is routinely used for obtaining a reference measurement, where the reference measurement may be performed before and/or during and/or after a biological sample measurement. For example, a reference solution can have a high KCl concentration. A reference electrode of a potentiometric sensor, which comprises a membrane specific for chloride, is brought in contact with the reference solution. The constant KCl concentration allows the reference electrode to return a constant signal as compared to a signal returned by a working electrode of the potentiometric sensor, which is in direct contact with a sample of interest. The reference electrode may be placed in a fluidic conduit in close proximity to the corresponding working electrode or in a dedicated reference fluidic conduit. Reference electrode and reference fluidic conduit may be part of the sensor assembly, whereby a sensor assembly may comprise a plurality of reference electrodes and/or reference fluidic conduits. Alternatively, reference electrode and reference fluidic conduit may be part of the IVD analyzer, where the reference electrode and reference fluidic conduit are in operative connection with the corresponding working electrodes and fluidic conduits of the sensor assembly, respectively.

A "stand-by solution/rinse solution" is a solution that is used to rinse the sensor after sample measurement has been performed and is kept in contact with the sensor until it is replaced by another type of sample.

A "wetting solution" is a solution that is used to initialize a new, unwetted sensor. This procedure is usually performed when a new sensor or a new set of sensors are taken into operation, e.g., after insertion into the IVD analyzer. It is a required procedure to ensure reliable operation of each sensor. The sensors are thereby contacted with wetting solution for a predetermined time. No sample measurements are performed during the wetting procedure.

A "cleaning solution" is a solution that is used to rinse and clean the fluidic system and sensors after measurement of a sample. In order to enhance the cleaning solution's efficacy in removing traces of previous sample material or debris, etc., it may comprise certain additives, e.g., detergents, sodium hypochlorite, biocide, etc.

The above-mentioned types of solutions may have different compositions or they may have partially or entirely the same compositions. Their naming therefore reflects their function. For example, a wetting solution may have the same composition as a stand-by solution, however it is used for a different purpose and in a different manner.

The term "parameter" is herein used as general term indicating a constituent of a sample or a physical or chemical characteristic of a sample that can be determined and analyzed with suitable methods. For example, the term "parameter" can refer to an analyte, which is any substance or compound in a sample that an analytical method or test seeks to detect (e.g., chemical elements like ions, or molecules like peptides, proteins, RNA, DNA, fatty acids, carbohydrates and the like). It can also refer to physical or chemical characteristics of a sample, e.g., color, temperature, turbidity, viscosity, acidity, alkalinity, etc. In general, the information on presence, absence, concentration and/or the properties of a sample parameter may give an indication on the health status of a patient and thus may be used to derive a diagnosis, or it may be used to determine and regulate a therapeutic regimen. Further, a known analyte level may be used in, e.g., a QC sample or calibrator in order to confirm that an IVD analyzer is still operating within specifications or admissible range. Examples of parameters of interest in the context of this disclosure are the partial pressure of gases, such as $PO_2$ and $PCO_2$, oxygen saturation ($SO_2$), blood electrolytes such as sodium ($Na^+$), potassium ($K^+$), magnesium ($Mg^{2+}$), calcium ($Ca^{2+}$), lithium ($Li^+$), chloride ($Cl^-$), protons ($H^+$) in relation to pH, bicarbonate values ($HCO_3^-$), and metabolites such as glucose, lactate, urea, creatinine. Other parameters of interest are hemoglobin, hemoglobin derivatives, such as deoxygenated hemoglobin, oxyhemoglobin, carboxyhemoglobin, methemoglobin, sulfhemoglobin, and bilirubin. An example of a physical parameter of interest is the hematocrit level.

In order to perform an analytical measurement based on electrochemical measuring principles, e.g., in blood gas and electrolyte testing, one or more electrochemical sensors need to be brought into contact with a sample. The term "electrochemical sensor" thereby comprises any type of sensor that converts a (bio)chemical reaction into an electrical signal. Different measuring principles may be applied depending on the parameter to be measured. For example, electrolytes or ions can be determined by potentiometric measurement principles. Potentiometric sensors measure the potential or voltage between two electrodes in a solution. A potentiometric sensor therefore usually comprises at least a working electrode (also referred to as measuring electrode) and a reference electrode. In this disclosure, the term "potentiometric working electrode" (PWE) is used to describe the working electrode in a potentiometric sensor. Analogously, the term "potentiometric reference electrode" (PRE) refers to the reference electrode of a potentiometric sensor. A membrane that is sensitive to a specific electrolyte or ion is arranged between the sample and the working electrode. The membrane usually has a complex composition comprising, e.g., polymers, plasticizers, ionophores, and lipophilic salts. Ionophores are a class of compounds that reversibly bind ions thereby increasing the membrane's permeability to a specific ion of interest and are selected according to the parameter to be measured by the sensor. The ion of interest is able to cross the membrane, thereby creating a change of potential, which is detected by the working electrode. The reference electrode on the other hand is in direct contact with a reference solution, which itself is in contact with the sample (liquid junction), thus no sample induced change of potential is established. In this way, the reference sensor returns a constant signal independent of the ion concentration in the sample. The difference in voltage between the reference and working electrode is then used to calculate the concentration of the ion of interest in solution. In fact, the difference in voltage between the electrodes is proportional to the logarithm of the concentration of the ion of interest. Since these types of sensors are ion-selective, they are also referred to as ion-selective electrodes. They enable the measurement of many parameters, e.g., potassium ($K^+$), sodium ($Na^+$), calcium ($Ca^{2+}$), chloride ($Cl^-$), magnesium ($Mg^{2+}$), lithium ($Li^+$), etc., and/or the determination of chemical properties of a sample, e.g., by determining the sample's pH-value. The potentiometric measurement principle does however not only allow measurement of electrolytes or ions, but is also used to determine blood gas levels, e.g., $PCO_2$ (with a Severinghaus-type sensor), and/or metabolites, e.g., urea, ammonium. Apart from the working electrode and the reference electrode, a potentiometric sensor may comprise further correction electrodes for correcting potential background noise or interferences. Further, a potentiometric sensor may comprise an electrode complemented with a specific enzyme, i.e., the enzyme is applied to the electrolyte layer or electrolyte fluid between the membrane and the electrode. For example, Severinghaus-type sensors comprise carbon anhydrase, which in the presence of water catalyzes the hydration of carbon dioxide into hydrogen carbonate.

Another electrochemical measuring principle is the amperometric measurement principle. An amperometric sensor measures the flow of electric current between two electrodes, whereby the electric current is generated by oxidation/reduction reactions. An amperometric sensor therefore usually comprises at least a working electrode (also referred to as measuring electrode) and a counter electrode. In such a two-electrode arrangement, the counter electrode also functions as a reference electrode to act as a reference in measuring and stabilizing the potential of the working electrode. Therefore, the term "amperometric working electrode" (AWE) is used to describe the working electrode of an amperometric sensor and the term "amperometric counter reference electrode" (ACRE) is used to describe an electrode acting both as counter and reference electrode in an amperometric sensor. However, the reference electrode may also be implemented as a separate electrode aside from a working and counter electrode. In consequence, the electrodes of such an arrangement will be referred to as an "amperometric working electrode" (AWE), an "amperometric counter electrode" (ACE), and an "amperometric reference electrode" (ARE) in this disclosure.

In the IVD field, different types of amperometric sensors are used. For example, a sensor for measuring partial pressure of oxygen ($PO_2$) may function according to the Clark measurement principle, in which oxygen diffuses through a membrane to a working electrode that is kept at a constant negative voltage in relation to the counter reference electrode. The oxygen is reduced at the working electrode, inducing an electric current between the working electrode and the counter reference electrode. The current can be measured and is proportional to the oxygen contained in the sample. Other types of amperometric sensors comprise enzyme-coupled electrodes, where the enzymes accelerate certain desired reactions. For example, certain glucose sensors based on glucose oxidase catalyze the conversion of glucose in the presence of water and oxygen to hydrogen peroxide and gluconic acid. The working electrode is held at a constant voltage relative to the reference electrode, which oxidizes the hydrogen peroxide, decomposing it to hydrogen ions, oxygen, and electrons. This induces a current that can be measured and is proportional to the glucose concentration in the sample. These sensors are also referred to as biosensors, due to the application of enzymes. Apart from measuring $PO_2$ and glucose, amperometric sensors can be also used to measure other metabolites, e.g., lactate, creatinine, creatine, etc.

By forming the reference and counter electrodes (PRE(s) and/or the ACRE(s) and/or the ARE(s) and the ACE(s)) on the same substrate and forming working electrodes (PWE(s) and/or the AWE(s)) on the opposite substrate a simpler and space-saving geometry of the sensor assembly is achieved. In addition, the arrangement enables a direct flow of current across the entire electrode surface and a symmetrical and homogenous distribution of the electrical field during measurements as opposed to the asymmetric, curved electrical field seen in prior art sensor arrangements. An asymmetrical electrical field and inhomogeneous current density can lead to a non-uniform attrition of the electrode surface, resulting in areas of different impedance on the electrode, which can have a negative effect on measurement accuracy and reliability. Further, the proposed arrangement simplifies the manufacturing process, since higher manufacturing tolerances can be accepted. For example, in a lateral sensor arrangement, a working electrode and a counter electrode of an amperometric sensor are typically formed adjacent to each other. However, slight misalignment of the electrodes can have a great adverse effect on the sensor's performance and therefore needs to be prevented. In contrast, forming the electrodes of a sensor on two opposite substrates tolerates a certain misalignment without reducing the sensor's performance.

According to certain embodiments, the sensor assembly comprises at least one conductivity sensor comprising a pair of electrodes for measuring conductivity of the sample, wherein the electrodes are formed on opposite substrates. Conductivity sensors are usually less complex than the above mentioned potentiometric or amperometric sensors. For example, they typically do not contain an ion-selective membrane. A conductivity sensor typically comprises identically constructed electrodes and is used to measure the ability of a solution to conduct an electrical current. The electrical current increases in proportion to the number of ions (or charged particles) dissolved in the solution, their electrical charge and their mobility. A conductivity sensor may be used, e.g., for detecting the presence or absence of a sample or other fluid in a fluidic conduit, for determining parameters (e.g., the hematocrit level in a sample), for detecting air bubbles or clots in a sample, or for calibration purposes. In prior art sensor assemblies, the electrodes of a conductivity sensor are typically arranged at the beginning and at the end of a fluidic conduit, with further sensors placed in between, in order to measure conductivity of an introduced sample along the fluidic conduit. This setup however has the disadvantage that the conductivity measurement may interfere with sensors operating between the conductivity electrodes and vice versa. Also, a potential ion concentration gradient or inhomogeneities due to trapped air bubbles within the sample may lead to undesired deviations and wrong hematocrit values. Arranging the conductivity electrodes opposite to each other allows for precise conductivity measurement. When placed in proximity to, e.g., a glucose sensor, it may enable a precise hematocrit determination adjacent to the place of glucose measurement. Abnormal hematocrit levels might interfere with blood glucose measurements and are therefore an indicator for interpreting glucose measurement results.

According to an embodiment, at least one substrate is at least in part transparent for enabling optical detection. The term "optical detection" as used herein generally refers to any photometric or spectroscopic measuring method that is suitable for the optical detection of sample parameters, e.g., the transmission of light through a sample or emission of light from an illuminated sample. Typical optical detection methods are, e.g., photometry, fluorescence spectroscopy, turbidimetry, fluorescence polarization, etc. Samples may be analyzed as such or after being diluted with another solution or after having been mixed with reagents. Optical detection methods may be used to detect the result of a chemical or biological reaction or to monitor the progress of a chemical or biological reaction. In order to perform an optical detection method on a sample that has been introduced into the fluidic conduit of a sensor assembly, at least one of the two opposite substrates is in part transparent. It may be made entirely of a transparent or translucent material (e.g., polypropylene, acrylic, polycarbonate, glass or the like) or it may contain transparent regions or recesses (optical measuring windows). For example, a metal substrate may have one or more recesses in the region of the fluidic conduit. This allows a light source that is installed in the IVD analyzer to illuminate the sample in the fluidic conduit. A photoreceptor detects the transmitted or emitted light from the sample, converting the electro-magnetic energy into an electrical signal. Examples for photoreceptors are, photodiodes, including avalanche photodiodes, phototransistors, photoconductive detectors, linear sensor arrays, CCD detectors, CMOS optical detectors, including CMOS array detectors, photomultipliers, photomultiplier arrays, etc. The combination of light source and photoreceptor is also regarded as sensor in the sense of this application.

According to certain embodiments, at least one substrate is thermally conductive or at least one thermally conductive element is arranged adjacent to at least one of the substrates for regulating operating temperature in the fluidic conduit. "Operating temperature" as used herein refers to the temperature or temperature range inside the fluidic conduit that provides optimal conditions to perform a sample measurement for a parameter of interest. For example, when determining $PO_2$, operating temperature is set to approximately 37° C. Other sensor types may require other operating temperatures. For that reason, a controlled transfer of heat to or from the fluidic conduit may be established. Operating temperature may be regulated indirectly via the IVD analyzer that is equipped with the units required to transmit heat to or remove heat from the sensor assembly, e.g., by a heating coil, a Peltier element, a heat sink and the like. The sensor assembly is installed in the IVD analyzer so that the temperature regulating units of the IVD analyzer are in direct contact with a thermally conductive substrate or a thermally conductive element of the sensor assembly. The thermally conductive element may be permanently attached to at least one substrate or it may be integrated into the housing of the sensor assembly. The surface of the thermally conductive element may cover a plurality of substrates, it may cover the entire major surface area of a single substrate, or it may partially cover a single substrate, e.g., confined to a certain region of a fluidic conduit. A substrate may be provided with a plurality of thermally conductive elements, if different regions in the fluidic conduit require different operating temperatures or if multiple fluidic conduits are available that require individual temperature-control. A thermally conductive element may be, e.g., a metal element or a metal alloy element, or any other suitable material. Alternatively, the thermally conductive element may be designed to actively regulate temperature, e.g., if it is a Peltier element. In this case, the IVD analyzer may actuate the thermally conductive element by providing electrical power via corresponding electrical contact points on the sensor assembly.

According to an embodiment, the PWE and the PRE of a potentiometric sensor are formed on the opposite substrates so that they are situated directly opposite to each other and/or wherein the AWE and the ACRE or the AWE and the ACE of an amperometric sensor are formed on the opposite substrates so that they are situated directly opposite to each other. For example, the working electrode of a glucose sensor (amperometric sensor) may be formed on a first substrate, the counter electrode of the glucose sensor on a second substrate, where the substrates are arranged so that the two electrodes are positioned directly opposite to each other, i.e., as close to each other as possible. The height of the fluidic conduit that runs between them thereby determines the distance from working electrode to counter electrode.

According to another embodiment, the at least one PWE is arranged in a first fluidic conduit and the at least one PRE is arranged in a reference fluidic conduit different from the first fluidic conduit. In order to achieve a more stable electric potential at the reference electrode of a potentiometric sensor, the reference electrode is typically exposed to a reference solution with a known ion concentration, e.g., highly concentrated KCl solution, as opposed to performing a reference measurement with, e.g., a biological sample. Therefore, the reference electrode is positioned in a separate reference fluidic conduit that enables providing a reference solution to the reference electrode while the working electrode is in contact with the sample of interest. A plurality of working electrodes of different potentiometric sensors may thereby share the same reference electrode or each working electrode may correspond with separate reference electrodes. As an alternative to arranging the reference fluidic conduit in an IVD analyzer, it can also be integrated into the sensor assembly. A sensor assembly may comprise a plurality of reference fluidic conduits if required.

According to an embodiment, the PRE and the ARE can be the same electrode. The reference electrode may therefore be arranged in the same fluidic conduit as the PWE and the AWE or it may be arranged in a separate reference fluidic conduit, inside or outside of the sensor assembly. In any case, the reference electrode is in operative connection with any of the potentiometric and amperometric working electrodes According to an embodiment, the sensor assembly further comprises a plurality of fluidic conduits and a plurality of sensors in each fluidic conduit wherein the plurality of sensors in each fluidic conduit are the same respectively. The additional fluidic conduits may serve as substitutes for a first fluidic conduit. Therefore, each fluidic conduit is equipped with the same set of sensors. In a first stage, measurements are only performed in a first fluidic conduit, i.e., samples of interest are introduced into the first fluidic conduit where measurements are conducted, while all other available fluidic conduits are blocked. A substitute fluidic conduit is made available only when sensors in the first fluidic conduit have been detected to be out of specification or have reached the end of their in-use time. Once such an incident occurs, the first fluidic conduit is blocked and prevented to be used for additional measurements while a second fluidic conduit is enabled for measuring samples. In anticipation of a sensor in the first fluidic conduit falling out of specification or reaching the end of its in-use time, the wetting procedure for the substitute fluidic conduit may be initiated while the first fluidic conduit is still in use. Sensor ageing or deterioration may be detected by monitoring a signal output or signal behavior, e.g., a signal slope or a signal drift, generated by the sensor during sample measurements and comparing the signal output to reference signals and/or reference ranges. Once a signal output reaches a predetermined threshold, the sensor is considered to be approaching the end of its in-use time. Ageing or deterioration may further be detected in the context of calibration procedures. The wetting procedure comprises providing a wetting solution to the substitute fluidic conduit to initiate the corresponding sensors, thus ensuring a seamless transition from the first fluidic conduit to the substitute fluidic conduit. This concept is expandable to even more fluidic conduits. Switchable valves may be used to direct samples into the appropriate fluidic conduit. Such valves can be installed either in the IVD analyzer or they can be integrated into the sensor assembly. In an example, access to the fluidic conduits may be regulated by controlling physical obstructions installed in the fluidic conduits, e.g., gas or liquid pouches, movable flaps, shutter-like constructions, etc. The physical obstructions may be controlled by establishing mechanical connections with counterparts in the IVD analyzer or they may be controlled by conductive or magnetic mechanism or they may be controlled by any other suitable mechanism. Providing substitute fluidic conduits allows for a longer in-use time of the sensor assembly.

According to another embodiment, the at least one AWE and the at least one ACRE or the at least one ACE and ARE are arranged in a second fluidic conduit different from the first fluidic conduit and different from the reference fluidic conduit. The sensors are distributed between the plurality of fluidic conduits based on their measuring principle and/or based on their frequency of use. For example, potentiometric sensors are arranged in a first fluidic conduit and amperometric sensors are arranged in a second fluidic conduit. It can be advantageous to group measurable parameters into "panels", based on their frequency of use in clinical settings. For example, physicians more often request determination of blood gas parameters together with electrolytes. However, metabolites, e.g., glucose or lactate, may be requested less frequently. It may therefore be advantageous to physically separate sensors measuring parameters of different panels in a sensor assembly. Preventing sensors from unnecessarily coming in contact with sample material prevents unnecessary deterioration and thus extends their in-use time. Furthermore, a separation prevents any potential measurement interferences between sensors of different measuring types.

According to yet another embodiment, the sensor assembly comprises potentiometric sensors and/or amperometric sensors with different susceptibility to deterioration when coming in contact with samples or other fluids, wherein the potentiometric sensors and/or the amperometric sensors with a higher susceptibility to deterioration are arranged along a first fluidic conduit and the potentiometric sensors and/or amperometric sensors with a lower susceptibility to deterioration are arranged along a fluidic conduit different from the first fluidic conduit. It is known that sensors can deteriorate over time. If a calibrated sensor is out of specification or admissible range repeatedly and cannot be brought back into specification through calibration, the sensor is no longer reliable and needs to be replaced. With other words, the sensor has reached the end of its in-use time. The rate of deterioration is highly dependent on the sensor's architecture, e.g., on the type of ionophores applied for ion-selective electrodes. This naturally occurring deterioration can be predicted and taken into account when determining the sensor's expected in-use time. However, there are other factors that influence the rate of deterioration in an unpredictable way and may deteriorate a sensor at a faster rate than predicted, e.g., if a sensor has a high susceptibility to a certain compound in a liquid (e.g., in a reagent or a cleaning solution). In this disclosure, such sensors are referred to as having a "higher susceptibility to deterioration", as compared to sensors that are unaffected or minimally affected by said liquid, herein referred to as having "lower susceptibility to deterioration". For example, an enzyme-coupled sensor may be more susceptible towards a cleaning solution. Certain components of the cleaning solution, e.g., sodium hypochlorite, can interfere with and thereby denature the enzymes, thus progressively worsening the sensor's functionality in an unpredictable manner. The sensor's in-use time may become much shorter than anticipated, thereby also shortening the in-use time of the entire sensor assembly. Whereas the same cleaning solution may be ineffective or have a negligible effect towards sensors with a different architecture, e.g., a sensor for measuring sodium ($Na^+$). To increase the in-use time of the sensor assembly, it can be of advantage to prevent the sensors with higher susceptibility to deterioration from coming in contact with said interfering liquid. It can therefore be advantageous to arrange them in a separate fluidic conduit, different from the fluidic conduit containing the sensors with lower susceptibility to deterioration. Valves and/or separated fluidic pathways may be implemented to prevent said interfering liquid from contacting the sensors with higher susceptibility to deterioration, while at the same time allowing supply of said liquid to the sensors with lower susceptibility to deterioration. Alternatively, the sensors with higher susceptibility to deterioration can be formed in duplicates in two fluidic conduits. If the first sensor in the first fluidic conduit reaches the end of its in-use time, the second fluidic conduit can be used to perform sample measurements.

According to an embodiment, each of the plurality of fluidic conduits has a separate fluidic inlet and a separate fluidic outlet. According to another embodiment, at least two fluidic conduits have at least one common fluidic inlet and/or at least one common fluidic outlet. Fluidic connection has to be established between the sensor assembly and the IVD analyzer in order to enable the transfer of samples to and from the fluidic conduit(s) of the sensor assembly. The IVD analyzer is therefore equipped with counterparts that tightly connect to the available fluidic inlet(s) and fluidic outlet(s) of the sensor assembly. In case of a sensor assembly with a plurality of fluidic conduits, each fluidic conduit may have a separate fluidic inlet and separate fluidic outlet. Alternatively, the fluidic conduits may converge inside the sensor assembly to share a common fluidic inlet and/or a common fluidic outlet.

According to an embodiment, the sensor assembly can comprise at least one switchable valve for directing the sample in any of the fluidic conduits. The switchable valve is in operative connection with the IVD analyzer. The controller of the IVD analyzer can thus control the switchable valve and thereby direct an available sample into the fluidic conduit(s) of choice.

According to an embodiment, the potentiometric sensor is a sodium or potassium or calcium or chloride or pH or carbon dioxide or urea or ammonium or lithium or magnesium sensor and the amperometric sensor is a glucose or lactate or creatinine or creatine or oxygen sensor.

In order that the embodiments of the present disclosure may be more readily understood, reference is made to the following examples, which are intended to illustrate the disclosure, but not limit the scope thereof.

FIG. 1 schematically shows an example of a sensor assembly 1 in a three-dimensional exploded-view. The sensor assembly comprises two opposite substrates 10A, 10B. One of the two opposite substrates 10B comprises a recess that forms fluidic conduits 2, 4 (indicated by dotted lines). Alternatively, the opposite substrates 10A, 10B may comprise complementary recesses that form the fluidic conduits 2, 4 when assembled (not shown). A sealing element may be positioned between the two opposite substrates 10A, 10B for sealing the fluidic conduits 2, 4 and preventing leakage (not shown). The sealing element may be a polymer with appropriate characteristics regarding viscosity and elasticity (e.g., an elastomer like a thermoplastic elastomer, rubber, silicone, latex, etc.). The first substrate 10A is a steel substrate and the opposite substrate 10B is a transparent polymer substrate. Electrodes 11A, 12A, 13A are formed on the steel substrate 10A. An insulation layer (not shown) is present between the electrodes 11A, 12A, 13A and the steel substrate 10A. Alternatively, both substrates may be made of an electrically non-conductive material, e.g., a polymer, a ceramic, a glass material, or both substrates may be made of an electrically conductive material, e.g., a metal or a metal alloy.

When the sensor assembly 1 is positioned in the in vitro-diagnostic (IVD) analyzer, the steel substrate 10A, that is thermally conductive, comes in operative connection with a temperature regulating unit of the IVD analyzer, e.g., a heating coil, a Peltier element, a heat sink (not shown). The IVD analyzer controls the temperature-regulating unit according to a predetermined protocol to transfer heat to or from the fluidic conduits 2, 4 via the thermally conductive substrate 10A. Thereby, the operating temperature in the fluidic conduits 2, 4 can be regulated.

A plurality of sensors are arranged on the two opposite substrates 10A, 10B, facing the fluidic conduits 2, 4. In the embodiment depicted in FIG. 1, the sensor assembly 1 comprises amperometric sensors, potentiometric sensors, and conductivity sensors. The amperometric sensors comprise amperometric working electrodes (AWE) 11A, amperometric counter electrodes (ACE) 11C, and amperometric reference electrodes (ARE) 11B. Amperometric sensors are used to detect a variety of sample parameters, e.g., $PO_2$, glucose or lactate. The potentiometric sensors in FIG. 1 comprise potentiometric working electrodes (PWE) 12A and potentiometric reference electrodes (PRE) 12B. Potentiometric sensors are used to detect parameters such as $PCO_2$, pH, $Na^+$, $Ca^{2+}$, $K^+$, and $Cl^-$, etc. The conductivity sensor in FIG. 1 comprises two electrodes 13A, 13B and is used to measure the ability of a sample to conduct an electrical current. This can be used to determine, e.g., the hematocrit level in a sample. The order in which the electrodes 11A, 11B, 12A, 12B, 13A, 13B are arranged on the two opposite substrates 10A, 10B can be based on different factors. For example, electrodes that potentially interfere with each other may be arranged as far apart from each other as possible. In particular, certain materials used for forming the sensory elements can leach between near-by sensory elements and thereby cause interferences. For example, the release of Ag ions from Ag/AgCl-electrodes may have an adverse effect on the stability of enzymes immobilized on the working electrode of amperometric sensors. In another example, leaching of enzymes from the working electrode of an amperometric sensor may have an adverse effect on the functionality of other amperometric working electrodes (e.g., a bovine-serum-albumin-working electrode may be contaminated by leaching of lactate oxidase and/or glucose oxidase from the lactate or glucose working electrode, respectively). In yet another example, leaching plasticizers and/or ionophores from ion-selective-electrode-membranes may have an adverse effect on the functionality of adjacently arranged potentiometric sensors. Electrodes that are based on the same measuring principle or that are operated in the same temperature range may be grouped together. In the embodiment shown in FIG. 1, the ARE 11B, the ACE 11C, and the PRE 12B are formed on the same substrate 10B, whereas the AWE 11A and the PWE 12A are formed on the opposite substrate 10A. The ACE 11C are thereby positioned to lie directly opposite to their corresponding AWE 11A when the two opposite substrates 10A, 10B are assembled. With regard to the conductivity sensor, a first electrode 13A is formed on a first substrate 10A, and a second electrode 13B is formed on the opposite substrate 10B.

Once a sample, e.g., a biological sample, a calibrator, a quality control (QC) sample, a reference solution, is introduced into the fluidic conduits 2, 4 via respective fluidic inlets 5, 7 it comes in contact with the electrodes 11A, 11B, 11C, 12A, 12B, 13A, 13B and a measurement can be performed. In the embodiment depicted in FIG. 1, the fluidic conduit 4 is a reference fluidic conduit and is designated for receiving reference solution in order to conduct reference measurements. The reference fluidic conduit 4 has a separate fluidic inlet 7 through which the reference solution is transported into the sensor assembly 1 from a reservoir in the IVD analyzer (not shown). The reference electrodes PRE 12B and ARE 11B are formed along the reference fluidic conduit 4. The first fluidic conduit 2 and the reference fluidic conduit 4 converge and lead into a common fluidic outlet 8, through which the fluid is transferred out of the sensor assembly 1 and back into the fluid system of the IVD analyzer, where it can be wasted (not shown). The fluidic inlets 5, 7 and the fluidic outlet 8 are depicted as apertures in FIG. 1. In order to establish fluidic connection with corresponding counterparts in the IVD analyzer, the fluidic inlets 5, 7 and the fluidic outlet 8 may however protrude from the substrate, e.g., in a tubular shape, forming the male part of a mating connector pair. The counterparts in the IVD analyzer may be designed as receptacles for the protruding tubular shapes. The tubular protrusions may be formed by the substrate 10B or they may be formed by a housing (not shown) that encloses the sensor assembly 1.

The electrical contact elements 14 are used to establish electrical connection between the sensors of the sensor assembly 1 and the IVD analyzer. In the embodiment as shown in FIG. 1, the electrodes 11A, 12A, 13A formed on a first substrate 10A are connected to the corresponding electrical contact elements 14 via electrically conducting pathways printed onto the substrate 10A, e.g., silver, silver chloride, platinum or carbon pathways. On the second substrate 10B, the electrodes 11B, 11C, 12B, 13B are connected to the corresponding electrical contact elements 14 through the substrate 10B via a through-hole, whereby the through-hole is filled with an electrically conductive material. Thus, the electrodes 11B, 11C, 12B, 13B and the electrical contact elements 14 are formed on the opposite major surface areas of the second substrate 10B. Alternatively, the electrical contact elements 14 may be formed on the same major surface area as the electrodes 11B, 11C, 12B, 13B and be connected via electrically conducting pathways printed onto the substrate.

When assembled during manufacturing, the two opposite substrates 10A, 10B are permanently attached to each other. This may be achieved, for example, with adhesive or by welding, or with mechanical fastening methods, such as snap lock mechanisms, screws, bolts and the like. The sensor assembly 1 further comprises a housing (not shown), typically made of an electrically non-conducting material, e.g., a polymer, to protect the sensors and wiring from external influences and to facilitate handling. The sensor assembly 1 including its housing is exchangeably insertable into a corresponding receiving unit of the IVD analyzer (not shown), where the analytical measurements are then performed.

Figure 2A:
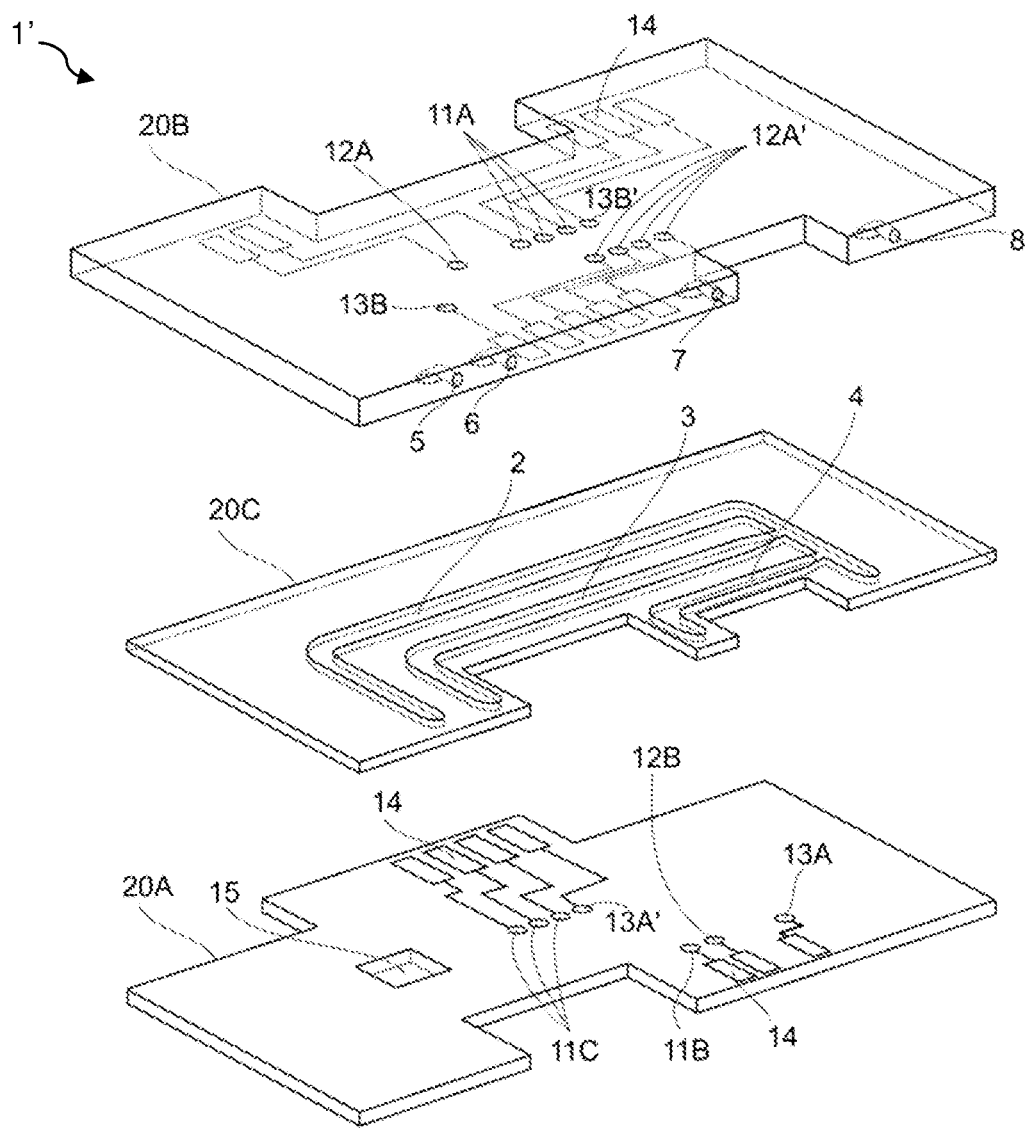
FIG. 2A is a schematic three-dimensional exploded-view of a sensor assembly according to further embodiments comprising two opposite substrates with a spacer in-between in accordance with an embodiment of the present disclosure.

FIG. 2A schematically illustrates another example of a sensor assembly 1' according to further embodiments of the present disclosure. The sensor assembly comprises two opposite substrates 20A, 20B. A spacer 20C is arranged in between the two opposite substrates 20A, 20B, where the spacer 20C comprises recesses that form fluidic conduits 2, 3, 4, of which one is a reference fluidic conduit 4. The spacer 20C is made of an inert, electrically non-conducting material, e.g., polymer, ceramic, or glass material. In addition, the spacer may have appropriate properties regarding viscosity and elasticity to ensure adequate sealing of the fluidic conduits 2, 3, 4. Alternatively, a sealing element may be arranged between the first one of the two substrates 20A and the spacer 20C and between the second one of the two substrates 20B and the spacer 20C for sealing the fluidic conduits 2, 3, 4 and preventing leakage (not shown). The first substrate 20A is a steel substrate and the second substrate 20B is a transparent polymer substrate. The steel substrate 20A enables the regulation of operating temperature in the fluidic conduits 2, 3, 4. It is therefore arranged such as to be placed in operative connection with a temperature-regulating unit of the IVD analyzer (not shown). The transparent polymer substrate 20B can enable optical detection of sample parameters of interest. An optical detection unit comprising, e.g., a light source and a photoreceptor, may be installed in the IVD analyzer (not shown). Once the sensor assembly 1' is positioned in the IVD analyzer, the optical detection unit is in alignment with one or more of the fluidic conduits 2, 3, 4. In the embodiment illustrated in FIG. 2A, the light source (not shown) is supposed to be positioned above the second substrate 20B, whereby the light source emits light directed through a sample in the first fluidic conduit 2, and whereby the transmitted light is detected by a photoreceptor (not shown) positioned below the first substrate 20A. The first substrate 20A therefore comprises an aperture 15 to allow the transmitted light to reach the photoreceptor. The aperture 15 is a recess formed in the first substrate 20A and filled with a transparent material, e.g., a polymer or glass. Alternatively, both the light source and the photoreceptor may be positioned on the same side of the sensor assembly 1', e.g., above the second substrate 20B. In an example, the optical detection method used to determine the oxygen levels in a sample can be based on fluorescence quenching. Thereby, a fluorescence signal inversely proportional to oxygen levels in the sample is detected by the photoreceptor and converted into an electric signal. The samples may have to be preprocessed, e.g., they may have to be mixed with a reagent prior to the measurement.

A plurality of sensors are arranged on the two opposite substrates 20A, 20B facing the fluidic conduits 2, 3, 4 formed in the spacer 20C. In this case, they are grouped based on their susceptibility to deterioration by a system fluid. Sensors with higher susceptibility to deterioration are arranged along a first fluidic conduit 2. In the embodiment illustrated in FIG. 2A, this refers to sensors measuring, e.g., pH, glucose, or lactate. Therefore, the corresponding working electrodes AWE 11A and PWE 12A, as well as the counter electrodes ACE 11C are formed along the first fluidic conduit 2. The counter electrodes ACE 11C are thereby formed on the first substrate 20A and the working electrodes AWE 11A and PWE 12A are formed on the opposite substrate 20B. Sensors with lower susceptibility to deterioration are arranged along a fluidic conduit 3 different from the first fluidic conduit 2. This refers to sensors measuring, e.g., $Na^+$, $Ca^{2+}$, $K^+$, and $Cl^-$. The corresponding working electrodes PWE 12A' are formed on the opposite substrate 20B. All reference electrodes ARE 11B and PRE 12B are formed on the first substrate 20A along the reference fluidic conduit 4, whereby a single amperometric reference electrode ARE 11B is in operative connection with a plurality of amperometric working electrodes AWE 11A and amperometric counter electrodes ACE 11C, and a single potentiometric reference electrode PRE 12B is in operative connection with a plurality of potentiometric working electrodes PWE 12A, 12A'. In the embodiment in FIG. 2A, the sensor assembly 1' comprises two pairs of conductivity sensors 13A, 13A', 13B, 13B'. Two electrodes 13A, 13A' are formed on the first substrate 20A and two electrodes 13B, 13B' are formed on the second substrate 20B. One pair of conductivity electrodes 13A', 13B' are formed on the two opposite substrates 20A, 20B so that they are positioned directly opposite to each other in a first fluidic conduit 2. They may be used for determining the hematocrit of a sample in close proximity or adjacent to a glucose sensor. The other conductivity electrodes 13A, 13B are formed in the reference fluidic conduit 4 and the second fluidic conduit 3, respectively, and may be used to detect presence or absence of a sample in the respective fluidic conduit. The electrical contact elements 14 in FIG. 2A are connected to the sensors via electrically conducting pathways printed onto the substrates 20A, 20B and represent the electrical contact points between the sensor assembly 1' and the IVD analyzer.

The sensor assembly 1' as illustrated in FIG. 2A comprises separate fluidic inlets 5, 6, 7 for each of the plurality of fluidic conduits 2, 3, 4, respectively, wherein one of the plurality of fluidic conduits 2, 3, 4 is a reference fluidic conduit 4 and is designated for receiving reference solution in order to conduct reference measurements. The plurality of fluidic conduits 2, 3, 4 converge and lead into a common fluidic outlet 8, through which fluids are transported out of the sensor assembly 1' and back into the fluid system of the IVD analyzer, where they can be wasted (not shown). The fluidic inlets 5, 6, 7 and the fluidic outlet 8 are formed in the second substrate 20B and merge into the fluidic conduits 2, 3, 4, respectively, in the spacer 20C. Alternatively, the fluidic inlets 5, 6, 7 and fluidic outlet 8 may be formed in the first substrate 20A and may merge into the fluidic conduits 2, 3, 4, respectively, from there, or they may be formed in the spacer 20C. As depicted in FIG. 2A, the fluidic connections between the sensor assembly 1' and the IVD analyzer are in parallel to the flow direction of the fluidic conduit, which reduces the risk of air bubbles forming at the interface and ensures a reliable rinsing or cleaning. However, the fluidic connection between sensor assembly 1' and IVD analyzer may be established at any angle between 0° and 90°.

Figure 2B:
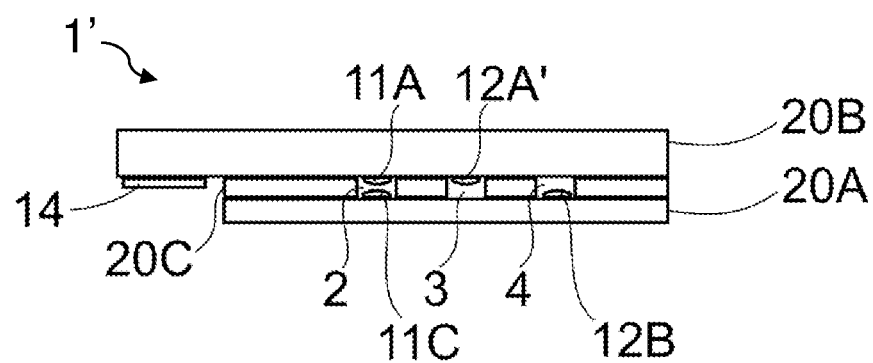
FIG. 2B schematically shows the sensor assembly of FIG. 2A in a lateral cross-section view in accordance with an embodiment of the present disclosure.

FIG. 2B is a schematic illustration showing a cross section through the sensor assembly 1' of FIG. 2A. The sensor assembly 1' is shown in an assembled form, i.e., the substrates 20A, 20B, and the spacer 20C are connected to each other. The AWE 11A and the ACE 11C of an amperometric sensor are formed on two opposite substrates 20B and 20A, respectively, so that they are situated directly opposite to each other in the first fluidic conduit 2, which enables a homogeneous and symmetrical current density and field distribution on the electrode surface during measurements. Further, the PWE 12A' and the PRE 12B of a potentiometric sensor are formed on two opposite substrates 20B and 20A, respectively, where the PWE 12A' faces the second fluidic conduit 3 and the PRE 12B faces the reference fluidic conduit 4. The contact element 14 connected to an electrode, e.g., AWE 11A, that is formed on substrate 20B is also indicated.

Figure 3:
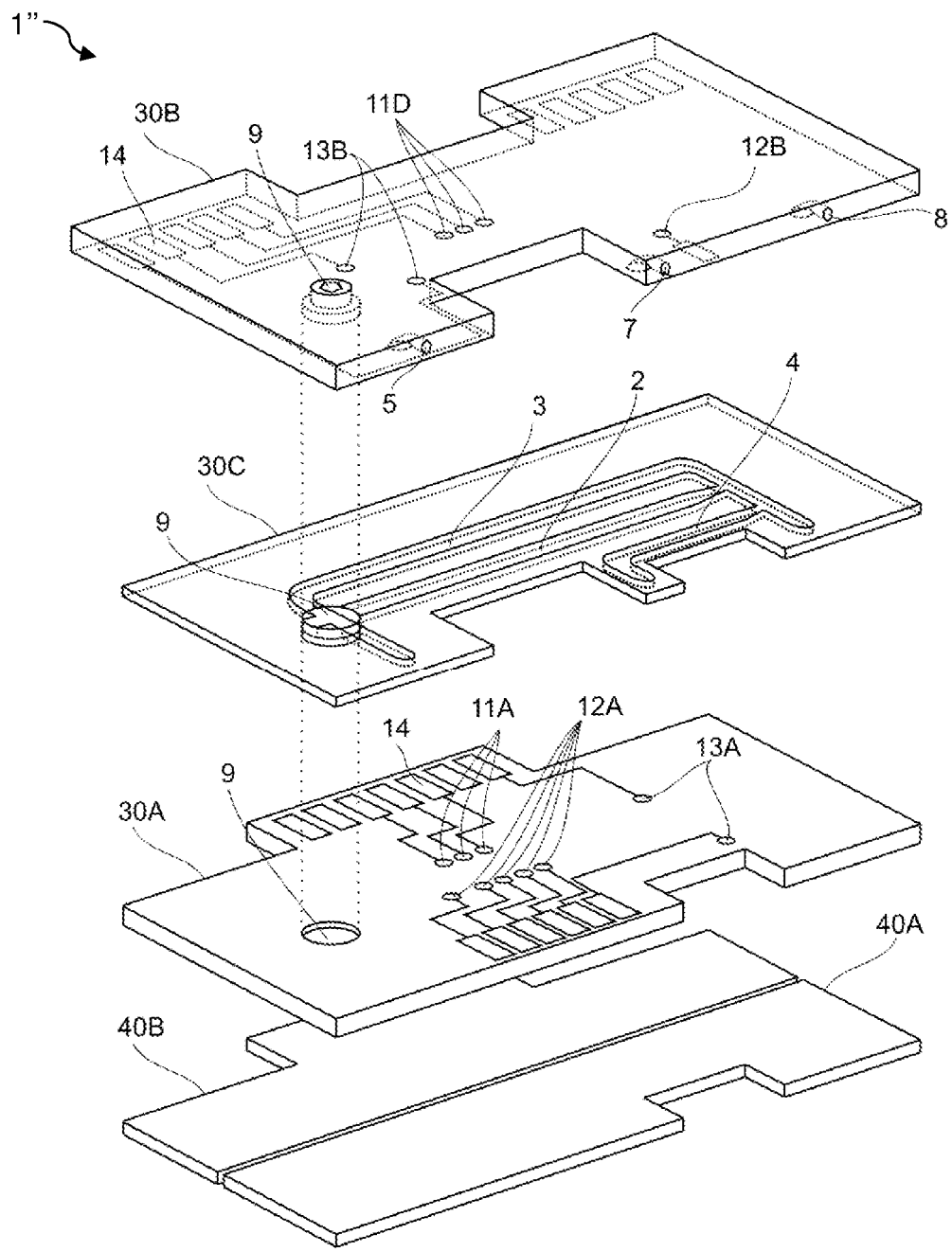
FIG. 3 is a schematic three-dimensional exploded-view of a sensor assembly according to further embodiments comprising two opposite substrates and a valve for directing fluids into any of the fluidic conduits in accordance with an embodiment of the present disclosure.

FIG. 3 schematically illustrates in a three-dimensional exploded-view yet another example of a sensor assembly 1" according to further embodiments of the present disclosure. The sensor assembly 1" comprises two opposite substrates 30A, 30B. A spacer 30C is arranged in between the two opposite substrates 30A, 30B, wherein the spacer 30C comprises recesses that form the fluidic conduits 2, 3 and the reference fluidic conduit 4. Both opposite substrates 30A, 30B are polymer substrates, whereby the second substrate 30B is made of a transparent polymer to enable optical detection of sample parameters of interest. The sensor assembly 1" further comprises thermally conductive elements 40A, 40B that are arranged adjacent to the first substrate 30A and that are made of a thermally conductive material, e.g., metal or a metal alloy. The sensor assembly 1" may comprise a single thermally conductive element or it may comprise a plurality of thermally conductive elements 40A, 40B. In the latter case, the plurality of thermally conductive elements 40A, 40B may be made of the same thermally conductive material, or they may be made of different materials with different characteristics regarding thermal conductivity. The thermally conductive elements 40A, 40B are in operative connection with separate temperature regulating units of the IVD analyzer (not shown), when the sensor assembly 1" is positioned in the IVD analyzer. This enables supply or extraction of heat to or from the fluidic conduits 2, 3, and the reference fluidic conduit 4 of the sensor assembly 1" via the thermally conductive elements 40A, 40B, independently. The setup as shown in FIG. 3 allows to regulate the operating temperature in a first fluidic conduit 2 and the reference fluidic conduit 4 by supplying or extracting heat via the first thermally conductive element 40A. The operating temperature in a second fluidic conduit 3 can be separately regulated by supplying or extracting heat via the second thermally conductive element 40B. An insulation layer may be implemented between the two thermally conductive elements 40A, 40B to prevent temperature exchange between them (not shown).

The two opposite substrates 30A, 30B comprise a plurality of sensors facing the fluidic conduits 2, 3 and the reference fluidic conduit 4 formed in the spacer 30C. In this case, they are distributed into different fluidic conduits based on their frequency of use in a clinical setting, i.e., the potentiometric working electrodes PWE 12A of potentiometric sensors are arranged along a first fluidic conduit 2 and the amperometric working electrodes AWE 11A and amperometric counter reference electrodes ACRE 11D are arranged along a second fluidic conduit 3 different from the first fluidic conduit 2 and the reference fluidic conduit 4. The potentiometric reference electrode PRE 12B is formed along the reference fluidic conduit 4. The PWE 12A and AWE 11A are thereby formed on the first substrate 30A, whereas the PRE 12B and the ACRE 11D are formed on the opposite substrate 30B. The single PRE 12B is in operative connection with the plurality of PWE 12A, thereby forming a plurality of potentiometric sensors for measuring, e.g., pH, $Na^+$, $Ca^{2+}$, $K^+$, and $Cl^-$. The plurality of AWE 11A and ACRE 11D form a plurality of amperometric sensors for measuring, e.g., glucose or lactate. The sensor assembly 1 further comprises two pairs of conductivity sensors 13A, 13B. Two electrodes 13A are formed on the first substrate 30A and are in operative connection with two electrodes 13B that are formed on the opposite substrate 30B. The electrical connection between the sensor assembly 1" and the IVD analyzer is established via the electrical contact elements 14. According to a further embodiment not illustrated in this disclosure, the same set of sensors may be formed in both the first fluidic conduit 2 and the second fluidic conduit 3. Sample measurements can be conducted in the first fluidic conduit 2 until, e.g., the first sensor in the first fluidic conduit 2 falls out of specification or reaches the end of its in-use time. In anticipation of the first sensor in the first fluidic conduit 2 falling out of specification or reaching the end of its in-use time, the wetting procedure for the second fluidic conduit 3 may be initiated while the first fluidic conduit 2 is still in use. The wetting procedure comprises providing a wetting solution to the second fluidic conduit 3 to initiate the corresponding electrodes 11A, 11D. After completion of the wetting procedure, sample influx may then be directed into the second fluidic conduit 3 while blocking access to the first fluidic conduit 2. Sample measurements can then be conducted in the second fluidic conduit 3 until, e.g., the first sensor in the second fluidic conduit 3 reaches the end of its in-use time. Only then would the sensor assembly 1" have to be replaced by the operator, thus increasing the in-use time of the sensor assembly 1".

The sensor assembly 1" as illustrated in FIG. 3 comprises two separate fluidic inlets 5, 7 that are formed in the second substrate 30B. A first fluidic inlet 7 leads into the reference fluidic conduit 4 that is formed in the spacer 30C. The second fluidic inlet 5 is a common fluidic inlet for a first fluidic conduit 2 and a second fluidic conduit 3. The first fluidic conduit 2, the second fluidic conduit 3, and the reference fluidic conduit 4 converge and lead into a common fluidic outlet 8, through which fluids are transported out of the sensor assembly 1" and back into the fluid system of the IVD analyzer, where they can be wasted (not shown). In order to direct the sample into the first fluidic conduit 2 or the second fluidic conduit 3 or into both fluidic conduits 2, 3 simultaneously, the sensor assembly 1" comprises a switchable valve 9, which is illustrated as rotatable valve in FIG. 3. It may however also be implemented as a flap or shutter-like element, etc., or a magnetically actionable element. In the embodiment depicted in FIG. 3, the valve 9 extends from the first substrate 30A through the spacer 30C to the opposite substrate 30B (indicated by the dotted lines), where it presents a point of mechanical or inductive contact for a counterpart in the IVD analyzer. When the sensor assembly 1" is positioned in the IVD analyzer, the valve 9 comes in operative connection with the respective counterpart in the IVD analyzer (not shown), which enables the valve 9 to be switched to a desired position. For example, in FIG. 3 the valve is switched to a position that enables a sample to be transferred into the second fluidic conduit 3, while at the same time blocking access to the first fluidic conduit 2. Depending on the position of the valve 9, the sample may be directed into the first fluidic conduit 2 only, or into both fluidic conduits 2, 3 at the same time.

In the preceding specification, devices and methods according to various embodiments are described in detail. The devices and methods may be embodied in many different forms and should not be construed as limited to the embodiments set forth and illustrated herein. It is therefore to be understood that the devices and methods are not to be limited to the specific embodiments disclosed and that modifications and other embodiments are intended to be included within the scope of the appended claims. Although specific terms are employed herein, they are used in a generic and descriptive sense only and not for purposes of limitation. Unless defined otherwise, all technical and scientific terms used herein have the same meaning as commonly understood by one skilled in the art to which the disclosure pertains. Although any methods and materials similar to or equivalent to those described herein can be used in the practice or testing of the methods, the typical methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B" and "A includes B" may refer both to a situation in which, besides B, no other element is present in A (i.e., a situation in which A solely and exclusively consists of B) or to a situation in which, besides B, one or more further elements are present in A, such as element C, elements C and D, or even further elements.

Also, reference throughout the specification to "one embodiment", "an embodiment", "one example" or "an example", means that a particular feature, structure or characteristic described in connection with the embodiment or example is included in at least one embodiment. Thus, appearances of the phrases "in one embodiment", "in an embodiment", "one example" or "an example", in various places throughout this specification are not necessarily all referring to the same embodiment or example.

Furthermore, the particular features, structures, or characteristics may be combined in any suitable combinations and/or sub-combinations in one or more embodiments or examples.

What is claimed is:

1. A sensor assembly for an IVD analyzer comprising: two opposite substrates with at least one fluidic conduit formed in between for receiving a sample; a plurality of electrochemical sensors arranged on the two opposite substrates facing the at least one fluidic conduit for coming in contact with the sample and determining sample parameters, the plurality of electrochemical sensors being chosen from the groups of amperometric sensors, potentiometric sensors or combinations thereof; wherein a potentiometric sensor comprises a potentiometric working electrode (PWE) and a potentiometric reference electrode (PRE); wherein an amperometric sensor comprises an amperometric working electrode (AWE) and an amperometric counter reference electrode (ACRE) or an AWE and an amperometric reference electrode (ARE) and an amperometric counter electrode (ACE); wherein the PRE(s) and/or the ACRE(s) and/or the ARE(s) and the ACE(s) are formed on the same one of the two substrates and wherein the PWE(s) and/or the AWE(s) are formed on the opposite one of the two substrates; and wherein the at least one AWE and the at least one ACRE or the at least one ACE and ARE are arranged in a second fluidic conduit different from the first fluidic conduit and different from the reference fluidic conduit.

2. The sensor assembly according to claim 1, wherein the at least one fluidic conduit is formed in a spacer arranged between the two opposite substrates.

3. The sensor assembly according to claim 1 further comprising at least one conductivity sensor comprising a pair of electrodes for measuring conductivity of the sample, wherein the electrodes are formed on opposite substrates.

4. The sensor assembly according to claim 1, wherein at least one substrate is at least in part transparent for enabling optical detection.

5. The sensor assembly according to claim 1, wherein at least one substrate is thermally conductive or wherein at least one thermally conductive element is arranged adjacent to at least one of the substrates for regulating operating temperature in the fluidic conduit.

6. The sensor assembly according to claim 1, wherein the PWE and the PRE of a potentiometric sensor are formed on the opposite substrates so that they are situated directly opposite to each other and/or wherein the AWE and the ACRE or the AWE and the ACE of an amperometric sensor are formed on the opposite substrates so that they are situated directly opposite to each other.

7. The sensor assembly according to claim 1, wherein the at least one PWE is arranged in a first fluidic conduit and the at least one PRE is arranged in a reference fluidic conduit different from the first fluidic conduit.

8. The sensor assembly according to claim 1, wherein the PRE and the ARE are the same electrode.

9. The sensor assembly according to claim 1 further comprising a plurality of fluidic conduits and a plurality of sensors in each fluidic conduit, wherein the plurality of sensors in each fluidic conduit are the same respectively.

10. The sensor assembly according to claim 1 further comprising potentiometric sensors and/or amperometric sensors with different susceptibility to deterioration through a system fluid, wherein the potentiometric sensors and/or the amperometric sensors with a higher susceptibility to deterioration are arranged along a first fluidic conduit and the potentiometric sensors and/or amperometric sensors with a lower susceptibility to deterioration are arranged along a fluidic conduit different from the first fluidic conduit.

11. The sensor assembly according to claim 9, wherein each of the plurality of fluidic conduits has a separate fluidic inlet and a separate fluidic outlet.

12. The sensor assembly according to claim 9, wherein at least two fluidic conduits have at least one common fluidic inlet and/or at least one common fluidic outlet.

13. The sensor assembly according to claim 12 further comprising at least one switchable valve for directing the sample in any of the fluidic conduits.

14. The sensor assembly according to claim 1, wherein the potentiometric sensor is a sodium or potassium or calcium or chloride or pH or carbon dioxide or urea or ammonium or lithium or magnesium sensor, and the amperometric sensor is a glucose or lactate or creatinine or creatine or oxygen sensor.

* * * * *